US012727829B2

(12) United States Patent
Ueki

(10) Patent No.: US 12,727,829 B2
(45) Date of Patent: Sep. 8, 2026

(54) SENSOR SYSTEM AND VEHICLE INCLUDING THE SAME

(71) Applicant: Murata Manufacturing Co., Ltd., Nagaokakyo (JP)

(72) Inventor: Daichi Ueki, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 259 days.

(21) Appl. No.: 18/644,162

(22) Filed: Apr. 24, 2024

(65) Prior Publication Data

US 2024/0268765 A1 Aug. 15, 2024

Related U.S. Application Data

(63) Continuation of application No. PCT/JP2022/043602, filed on Nov. 25, 2022.

(30) Foreign Application Priority Data

Dec. 10, 2021 (JP) ................................ 2021-200763

(51) Int. Cl.
*A61B 5/00* (2006.01)
*A61B 5/0205* (2006.01)
*A61B 5/05* (2021.01)

(52) U.S. Cl.
CPC .......... *A61B 5/7217* (2013.01); *A61B 5/0051* (2013.01); *A61B 5/0205* (2013.01); *A61B 5/05* (2013.01); *A61B 5/681* (2013.01)

(58) Field of Classification Search
CPC ... A61B 5/7217; A61B 5/0051; A61B 5/0205; A61B 5/05; A61B 5/681; A61B 5/1102;
(Continued)

(56) References Cited

U.S. PATENT DOCUMENTS

2013/0261415 A1* 10/2013 Ashe .................. A61B 5/14552 600/323
2017/0282828 A1 10/2017 Carenza et al.

FOREIGN PATENT DOCUMENTS

JP 2017-518511 A 7/2017
JP 2020-185378 A 11/2020
JP 2021-071326 A 5/2021

OTHER PUBLICATIONS

International Search Report and Written Opinion mailed on Jan. 24, 2023, received for PCT Application PCT/JP2022/043602, filed on Nov. 25, 2022, 8 pages including English Translation.

* cited by examiner

*Primary Examiner* — Abid A Mustansir
(74) *Attorney, Agent, or Firm* — XSENSUS LLP

(57) ABSTRACT

A sensor system and a vehicle including the sensor system are provided. The sensor system achieves a reduction of power consumption without changing detection accuracy. A sensor system includes a first sensor, a second sensor, and a signal processing apparatus. The first sensor emits electromagnetic waves to a measurement target, and detects the predetermined-displacement data of the measurement target. The second sensor detects data of vibrations, which occur in or are transmitted to at least one of the measurement target or the first sensor, or the predetermined-displacement data of the measurement target. On the basis of the detected pieces of data, an operation-sensor determination circuit determines a minimal necessary operation sensor which is to be operated in view of removal or attenuation of noise vibration data superimposed on the predetermined-displacement data. A sensor-power-supply management circuit supplies power only to the sensor determined as the operation sensor.

20 Claims, 5 Drawing Sheets

(58) Field of Classification Search
CPC ... A61B 5/6893; A61B 5/7203; A61B 5/7221; A61B 5/0507; G01S 7/40; G01S 7/497; G01S 13/86; G01S 17/86
See application file for complete search history.

(a)

(b)

SENSOR SYSTEM AND VEHICLE INCLUDING THE SAME

CROSS-REFERENCE TO RELATED APPLICATIONS

This application is a continuation of international application no. PCT/JP2022/043602, filed Nov. 25, 2022, and which claims priority to Japanese application no. 2021-200763, filed Dec. 10, 2021. The entire contents of both prior applications are hereby incorporated by reference.

TECHNICAL FIELD

The present disclosure relates to a sensor system, which emits electromagnetic waves and which receives reflected waves returning from a measurement target, and a vehicle including the sensor system.

BACKGROUND ART

A conventional sensor system includes a radio wave sensor, a vibration sensor, and a signal processing apparatus. The radio wave sensor transmits radio waves to an area for detection, receives radio waves obtained through reflection from an object, and outputs, to the signal processing apparatus, a radio wave sensor signal in accordance with the state of the object. The vibration sensor detects vibrations of either one or both of the radio wave sensor and the object, and outputs, to the signal processing apparatus, a vibration sensor signal corresponding to the detected vibrations. The signal processing apparatus attenuates vibration components, which are detected in the vibration sensor signal, from the radio wave sensor signal, and generates a signal which mainly contains components of the objects.

It has been proposed to provide multiple radio wave sensors and multiple vibration sensors in order to improve accuracy of detection of an object's state.

SUMMARY

Technical Problem

However, the conventional sensor system, tries to improve accuracy of detection of an object's state through acquisition of a large number of pieces of sensor information with use of multiple radio wave sensors and multiple vibration sensors. Therefore, in proportion to an increasing number of sensors, the power consumption of the sensor system of the related art is unfortunately increased.

Solution to Problem

The present disclosure is made to solve at least the issue described above, and provides a sensor system including one or more first sensors that emit electromagnetic waves to a measurement target, and that receive reflected waves to detect predetermined-displacement data of the measurement target. The reflected waves are obtained through reflection of the electromagnetic waves from the measurement target. One or more second sensors detect vibration data or the predetermined-displacement data. The vibration occurs in or is transmitted to at least one of the measurement target or the one or more first sensors. An operation-sensor determination circuit, on the basis of the predetermined-displacement data and the vibration data, determines a minimal necessary operation sensor which is to be operated in view of removal or attenuation of noise vibration data superimposed as noise on the predetermined-displacement data. A sensor-power-supply management circuit supplies power only to the operation sensor.

In the configuration, the operation-sensor determination circuit determines a minimal necessary operation sensor which is to be operated in view of removal or attenuation of noise vibration data superimposed on predetermined-displacement data of a measurement target, from among the one or more first sensors and the one or more second sensors. The sensor-power-supply management circuit supplies power only to the operation sensor determined by the operation-sensor determination unit.

Therefore, even when the sensor system includes multiple first and second sensors to improve accuracy of detection of the predetermined displacement of a measurement target, power is supplied, not to all the sensors, but only to the minimal necessary sensor which is to be operated in view of removal or attenuation of noise vibration data superimposed on predetermined-displacement data. Therefore, even when multiple first and second sensors are used to improve accuracy of detection of the predetermined displacement of a measurement target, the power consumption of the sensor system may be reduced without changing the detection accuracy.

The present disclosure provides a sensor system including one or more first sensors that emit electromagnetic waves to a measurement target, and that receive reflected waves to detect predetermined-displacement data of the measurement target. The reflected waves are obtained through reflection of the electromagnetic waves from the measurement target. One or more second sensors detect vibration data or the predetermined-displacement data. The vibration occurs in or is transmitted to at least one of the measurement target or the one or more first sensors. A noise-vibration removing circuit performs computation of removing or attenuating noise vibration data from the predetermined-displacement data on the basis of the predetermined-displacement data and the vibration data. The noise vibration data is superimposed as noise on the predetermined-displacement data. The computation is performed on a plurality of combinations from the one or more first sensors and the one or more second sensors, a plurality of combinations from the one or more first sensors, or a plurality of combinations from the one or more second sensors. An operation-sensor determination circuit determines any of the combinations as minimal necessary operation sensors which are to be operated in view of removal or attenuation of the noise vibration data. The any of the combinations derives a value closest to a true value of the predetermined-displacement data among a plurality of pieces of predetermined-displacement data obtained through removal or attenuation of the noise vibration data. A sensor-power-supply management circuit supplies power only to the operation sensors.

In the configuration, on the basis of the predetermined-displacement data and the vibration data which are detected by the first sensor(s) or the second sensor(s), computation of removing or attenuating, from the predetermined-displacement data, the noise vibration data superimposed as noise on the predetermined-displacement data is performed by the noise-vibration removing circuit on various combinations of sensors. The operation-sensor determination circuit determines, as minimal necessary operation sensors which are to be operated in view of removal or attenuation of noise vibration data superimposed on predetermined-displacement data, any combination, which derives a value closest to the true value of the predetermined displacement among multiple pieces of predetermined-displacement data obtained through removal of noise vibration data performed by the noise-vibration removing unit. The sensor-power-supply management circuit supplies power only to the combination of sensors determined as operation sensors by the operation-sensor determination unit.

Therefore, even when the sensor system includes multiple first and second sensors to improve accuracy of detection of the predetermined displacement of a measurement target, power is supplied, not to all the sensors, but only to minimal necessary sensors in view of removal or attenuation of noise vibration data superimposed on predetermined-displacement data. Therefore, even when multiple first and second sensors are used to improve accuracy of detection of the predetermined displacement of a measurement target, the power consumption of the sensor system may be reduced without changing the detection accuracy.

The present disclosure provides a vehicle including the sensor system described above.

The configuration enables a vehicle, which includes the sensor system achieving a reduction of power consumption, to be provided without changing accuracy of detection of the predetermined displacement.

Advantageous Effects

The present disclosure provides a sensor system and a vehicle including the sensor system. Even when multiple first and second sensors are used to improve accuracy of detection of predetermined displacement of a measurement target, the sensor system achieves a reduction of the power consumption without changing the detection accuracy.

DESCRIPTION OF EXEMPLARY EMBODIMENTS

An exemplary for implementing a sensor system of the present disclosure and a vehicle having the sensor system will be described.

Figure 1:
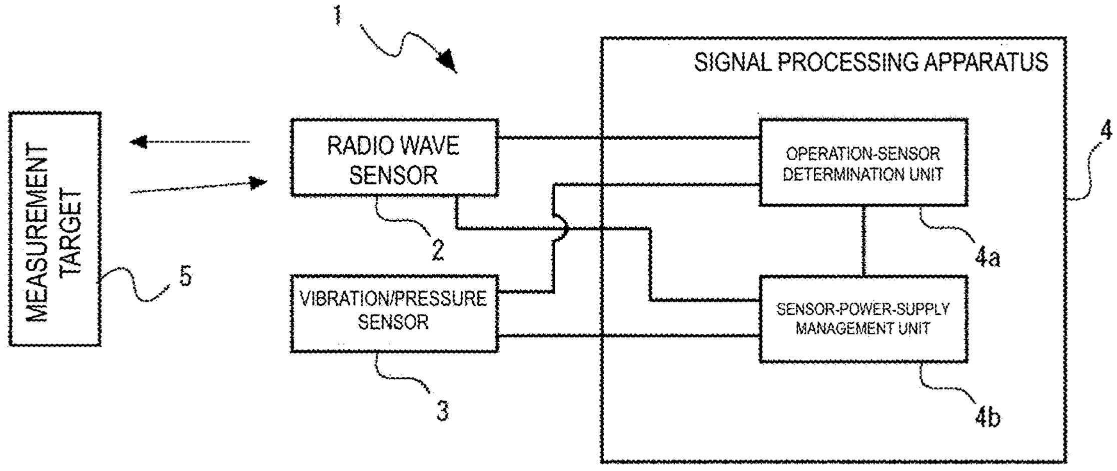
FIG. 1 is a block diagram illustrating the schematic configuration of a sensor system according to a first exemplary embodiment of the present disclosure.

FIG. 1 is a block diagram illustrating the schematic configuration of a sensor system 1 according to a first exemplary embodiment of the present disclosure. The sensor system 1 includes one or more first sensors 2, one or more second sensors 3, and a signal processing apparatus 4.

A first sensor 2 is, for example, a radio wave sensor. A radio wave sensor emits electromagnetic waves to a measurement target 5, and receives reflected waves obtained through reflection of the electromagnetic waves from the measurement target 5 (the reflected waves enter the radio wave sensor). The radio wave sensor detects, from the reflected waves, predetermined displacement of the measurement target 5, for example, body surface displacement of a human body, and outputs, to the signal processing apparatus 4, the detected predetermined-displacement data. The radio wave sensor is formed, for example, by a Doppler radar, a FMCW (Frequency Modulated Continuous Wave radar) radar, or a pulse radar. In the present exemplary embodiment, description will be made by taking, as radio waves, electromagnetic waves emitted by a radio wave sensor. In the present application, however, electromagnetic waves emitted by a radio wave sensor include sound waves and light waves and the like in a broad sense. Alternatively, a first sensor 2 is, for example, a pressure sensor. Alternatively, a first sensor 2 is, for example, a displacement sensor. Examples of a displacement sensor include a camera-type laser and an infrared laser.

A second sensor 3 is, for example, a vibration sensor or a displacement sensor. A vibration sensor is formed, for example, by a 6-axis inertial sensor or a vibration sensor such as a 3-axis acceleration sensor. A displacement sensor is formed by a displacement sensor such as a pressure sensor. Examples of a displacement sensor include a camera-type laser and an infrared laser. When a second sensor 3 is a vibration sensor, the second sensor 3 detects vibrations which occur in or are transmitted to either one or both of the measurement target 5 and the first sensor(s) (radio wave sensor(s)) 2. When a second sensor 3 is a displacement sensor, the second sensor 3 detects the predetermined displacement of the measurement target 5, for example, detects body surface displacement or the like of a human body from pressure received from the human body by the pressure sensor. In this case, the pressure sensor functions as a vital sensor which detects vital signs of the human body. The second sensor 3 outputs, to the signal processing apparatus 4, the detected vibration data, or the displacement data such as body surface displacement.

The signal processing apparatus 4 includes an operation-sensor determination unit **4*a* and a sensor-power-supply management unit 4*b*. The operation-sensor determination unit 4*a* determines an operation sensor(s) which is a minimal necessary sensor(s) that is to be operated in view of removal or attenuation of noise vibration data superimposed as noise on predetermined-displacement data of the measurement target 5. Specifically, any one of the first sensor(s) 2 or any one of the second sensor(s) 3, multiple first sensors 2, multiple second sensors 3, a combination of a first sensor 2 and a second sensor 3, or multiple combinations of a first sensor 2 and a second sensor 3 are determined. This determination is made on the basis of predetermined-displacement data detected from the first sensor(s) 2 and vibration data or predetermined-displacement data detected by the second sensor(s) 3. In the description below, the types of operation sensors which are determined by the operation-sensor determination unit 4*a*** are exemplary. Any type described above may be determined as an operation sensor.

Each of predetermined-displacement data, which is detected by the first sensor(s) 2, and vibration data or displacement data, which is detected by the second sensor(s) 3, contains either one or both of predetermined-displacement data of the measurement target 5 and noise-vibration component data which is superimposed on the predetermined-displacement data.

Assume the case in which both the first sensor(s) 2 and the second sensor(s) 3 detect no noise vibrations, for example, the case in which, in use of the sensor system 1 in a driver monitoring system (DMS), no noise vibrations are detected because the vehicle is in the idle state or is an electric vehicle. In this case, the operation-sensor determination unit 4*a* determines, as an operation sensor, only any one of the first sensor(s) 2 or any one of the second sensor(s) 3 which detects the predetermined displacement.

The operation-sensor determination unit 4*a* determines sensors, which are to be operated, according to a vibration removal method performed by a noise-vibration removing unit which is provided, as described below, downstream of the signal processing apparatus 4. An example of the vibration removal method is a removal method in which the noise-vibration removing unit, which is provided downstream, subtracts, from data detected by a sensor which detects both predetermined-displacement data and noise vibration data, data detected by a different sensor which detects noise vibration data. When the vibration removal method performed by the noise-vibration removing unit is a subtractive removal method in which noise vibration data is removed or attenuated as described above, if the total number of the first sensor(s) 2 and the second sensor(s) 3 is three or more, the operation-sensor determination unit 4*a* determines operation sensors as described below. That is, the operation-sensor determination unit 4*a* determines, as operation sensors, a combination of any one of the first sensor(s) 2 or any one of the second sensor(s) 3, which detects predetermined-displacement data and noise vibration data, and a different one of the first sensor(s) 2 or a different one of the second sensor(s) 3, which detects noise vibration data.

An exemplary vibration removal method may be a removal method in which the noise-vibration removing unit uses a blind source separation method to separate noise vibration data from predetermined-displacement data. When the vibration removal method is a blind source separation method, if the total of the first sensor(s) 2 and the second sensor(s) 3 is three or more, the operation-sensor determination unit 4*a* determines operation sensors as described below. That is, the operation-sensor determination unit 4*a* determines, as operation sensors, a combination of any one of the first sensor(s) 2 or any one of the second sensor(s) 3, which detects both predetermined-displacement data and noise vibration data, and a different one of the first sensor(s) 2 or a different one of the second sensor(s) 3, which detects both predetermined-displacement data and noise vibration data.

The sensor-power-supply management unit 4*b* supplies power only to the first sensor 2 or the second sensor 3, which is determined as an operation sensor by the operation-sensor determination unit 4*a*, or a combination of these. Therefore, power is not supplied to the remaining sensors, which are not determined as operation sensors. The power supply control may be exerted by the sensor-power-supply management unit 4*b* which directly controls on/off of power supply to the first sensor 2 or the second sensor 3, or the combination of these. Alternatively, the power supply control may be exerted by the sensor-power-supply management unit 4*b* which outputs, to each sensor, an instruction to switch on/off the power supply.

Figure 2:
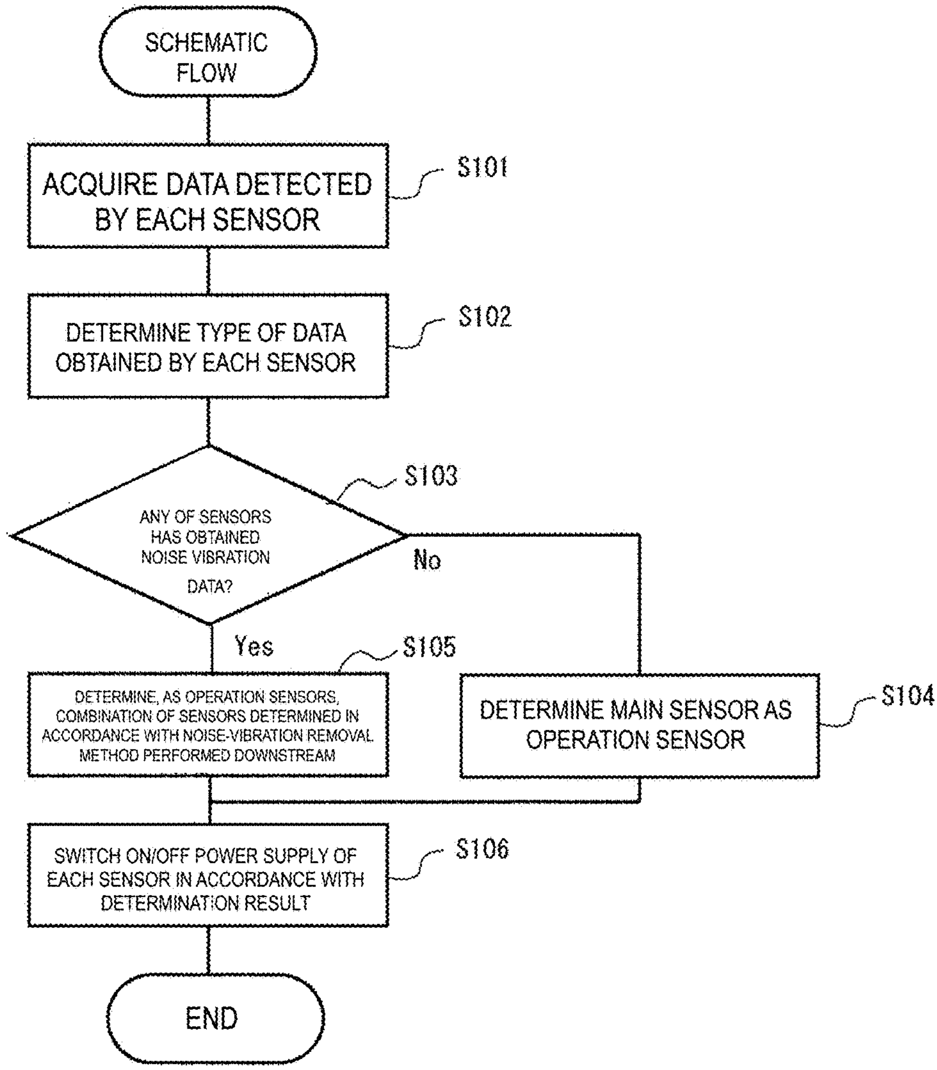
FIG. 2 is a flowchart of a power supply control process in a sensor system according to the first exemplary embodiment.

FIG. 2 is a flowchart of a power supply control process performed on the sensors in the sensor system 1 according to the first exemplary embodiment of the present disclosure. Steps S101 to S106 in the power supply control process are performed according to a computer program, which is stored in a memory included in the signal processing apparatus 4, by a CPU (central processing unit) included in the signal processing apparatus 4.

Detected-data acquisition step S101, in which data detected by each sensor is acquired, is first performed.

That is, each first sensor 2 obtains predetermined-displacement data of the measurement target 5, for example, body surface displacement data or the like from a human body, from reflected waves obtained through reflection, from the measurement target 5, of radio waves emitted from the radio wave sensor to the measurement target 5. The displacement data may contain noise vibration components caused by vibrations which occur in or are transmitted to either one or both of the measurement target 5 and the first sensor(s) 2. Each second sensor 3 obtains, for example, data of vibrations, which occur in or are transmitted to either one or both of the measurement target 5 and the first sensor(s) 2, or predetermined-displacement data of the measurement target 5, for example, body surface displacement data or the like of a human body. The obtained pieces of detected data are output from the first sensor(s) 2 and the second sensor(s) 3 to the operation-sensor determination unit 4*a*.

The operation-sensor determination unit 4*a* performs data-type determination step S102 in which the type of data obtained by each sensor is determined.

That is, the operation-sensor determination unit 4*a* regards, as a main sensor, a single sensor that detects displacement data closest to the true value of predetermined-displacement data and that is any one of the first sensor(s) 2 or any one of the second sensor(s) 3 which detects predetermined-displacement data of the measurement target 5. Predetermined-displacement data, which is detected by the main sensor when the measurement target 5 is motionless, is stored in advance as reference data in a memory. Alternatively, data, which is predetermined as predetermined-displacement data obtained from the measurement target 5 which is motionless, is stored in advance as reference data in the memory. The operation-sensor determination unit 4*a* determines, as sensors which detect the predetermined displacement such as body surface displacement, sensors, each of which has detected, in a particular frequency band, data having a high correlation with the reference data stored in the memory or data having similar statistics such as a kurtosis. The particular frequency band is a frequency band in which predetermined-displacement data is obtained. For example, when the predetermined-displacement data is body surface displacement data of a human body, the particular frequency band is the frequency band of 0 Hz to 10 Hz which includes that of breath and that of heartbeat, or the frequency band of 1 Hz to 10 Hz which includes only that of heartbeat.

Vibration data other than predetermined-displacement data in the particular frequency band, which is obtained when the main sensor is vibrating, is regarded as noise vibration data. In this case, among sensors other than the main sensor, sensors, each of which has detected, in the particular frequency band, data having a high correlation with the noise vibration data or data having similar statistics such as a kurtosis, are determined as sensors which detect noise vibration data superimposed on predetermined-displacement data.

Then, the operation-sensor determination unit 4*a* performs noise-vibration-detecting-sensor determination step S103 in which it is determined whether any of the sensors has obtained noise vibration data. That is, in data-type determination step S102, the operation-sensor determination unit 4*a* determines whether a sensor which has detected noise vibrations is present.

If the determination result of noise-vibration-detecting-sensor determination step S103 is No, which indicates that no sensors have obtained noise vibration data, in operation-sensor first-determination step S104, the operation-sensor determination unit 4*a* determines the main sensor as an operation sensor which is a minimal necessary sensor which is to be operated in view of removal or attenuation of noise vibration data superimposed on predetermined-displacement data.

If the determination result of noise-vibration-detecting-sensor determination step S103 is Yes, which indicates that a sensor which has obtained noise vibration data is present, in operation-sensor second-determination step S105, the operation-sensor determination unit 4*a* determines, as operation sensors, a combination of sensors determined in accordance with the noise-vibration removal method performed downstream.

That is, when the noise-vibration removal method performed downstream is the subtractive removal method described above, the operation-sensor determination unit 4*a* determines, as operation sensors, a combination of any one of the first sensor(s) 2 or any one of the second sensor(s) 3, which detects predetermined-displacement data and noise vibration data, and a different one of the first sensor(s) 2 or a different one of the second sensor(s) 3, which detects noise vibration data. When the noise-vibration removal method performed downstream is the blind source separation method described above, the operation-sensor determination unit 4*a* determines, as operation sensors, a combination of any one of the first sensor(s) 2 or any one of the second sensor(s) 3, which detects both predetermined-displacement data and noise vibration data, and a different one of the first sensor(s) 2 or a different one of the second sensor(s) 3, which detects both predetermined-displacement data and noise vibration data.

The sensor-power-supply management unit 4*b* performs sensor-power-supply setting step S106 in which the power supply of each sensor is switched ON or OFF in accordance with the determination result obtained by the operation-sensor determination unit 4*a*.

That is, when the operation-sensor determination unit 4*a* determines the main sensor as an operation sensor in operation-sensor first-determination step S104, the power supply of the main sensor is switched ON by the sensor-power-supply management unit 4*b*, and the power supplies of the remaining sensors are switched OFF by the sensor-power-supply management unit 4*b*. Alternatively, the power supplies of any combination of sensors, which is determined as operation sensors in operation-sensor second-determination step S105 in accordance with the noise-vibration removal method performed downstream, are switched ON by the sensor-power-supply management unit 4*b*, and the power supplies of the remaining sensors are switched OFF by the sensor-power-supply management unit 4*b*.

In the sensor system 1 according to the first exemplary embodiment, the operation-sensor determination unit 4*a* determines operation sensors which are minimal necessary sensors that are to be operated in view of removal or attenuation of noise vibration data superimposed on predetermined-displacement data of the measurement target 5, from among the one or more first sensors 2 and the one or more second sensors 3. The sensor-power-supply management unit 4*b* supplies power only to a first sensor 2 or a second sensor 3, which is determined as an operation sensor by the operation-sensor determination unit 4*a*, or a combination of these. Therefore, operations of sensors, which, in detection of the predetermined displacement of the measurement target 5, have no or slight influence on a result of detection of the predetermined displacement, are stopped.

Therefore, even when the sensor system 1 includes multiple first and second sensors 2 and 3 to improve accuracy of detection of the measurement target 5's predetermined displacement, power is supplied, not to all the sensors, but only to minimal necessary sensors that are to be operated in view of removal or attenuation of noise vibration data superimposed on predetermined-displacement data. Thus, even when multiple first and sensors 2 and 3 are used to improve accuracy of detection of the measurement target 5's predetermined displacement, for example, a human body's body surface displacement, the power consumption of the sensor system 1 may be reduced without changing the detection accuracy.

In the sensor system 1 according to the first exemplary embodiment, if the determination result of noise-vibration-detecting-sensor determination step S103 in FIG. 2 is No, which indicates that none of the first and second sensors 2 and 3 have detected noise vibration data, in operation-sensor first-determination step S104, the operation-sensor determination unit 4*a* determines, as an operation sensor, only a sensor that is any one first sensor 2 or any one second sensor 3 which detects the predetermined displacement and that is determined as the main sensor. The sensor-power-supply management unit 4*b* supplies power only to the single operation sensor. Therefore, the power consumption of the sensor system 1 may be further reduced without changing accuracy of detection of the measurement target 5's predetermined displacement.

In the sensor system 1 according to the first exemplary embodiment, any one combination from the first sensor(s) 2 and the second sensor(s) 3, whose total is three or more, is determined as operation sensors in operation-sensor second-determination step S105 in accordance with the subtractive removal method. Such a combination enables the sensor system 1 to detect the predetermined displacement of the measurement target 5 without changing the detection accuracy and with low power consumption. In this case, the noise-vibration removing unit provided downstream subtracts, from combined data of predetermined-displacement data and noise vibration data which are detected by any sensor determined as an operation sensor, noise vibration data detected by another sensor. Thus, noise vibration data is removed or attenuated from predetermined-displacement data of the measurement target 5.

In the sensor system 1 according to the first exemplary embodiment, a combination of any single sensor and a different sensor among the first sensor(s) 2 and the second sensor(s) 3, whose total is three or more, is determined as operation sensors in operation-sensor second-determination step S105 in accordance with the blind source separation method. Such a combination enables the sensor system 1 to detect the predetermined displacement of the measurement target 5 without changing the detection accuracy and with low power consumption. In this case, the noise-vibration removing unit provided downstream applies the blind source separation method to combined data of predetermined-displacement data and noise vibration data, which are detected by any sensor determined as an operation sensor, and to combined data of predetermined-displacement data and noise vibration data, which are detected by another sensor. This method is applied to separate predetermined-displacement data on the basis of the difference in magnitude of superimposed noise vibration components of the sensors, causing removal or attenuation of noise vibration data from predetermined-displacement data of the measurement target 5.

Figure 3:
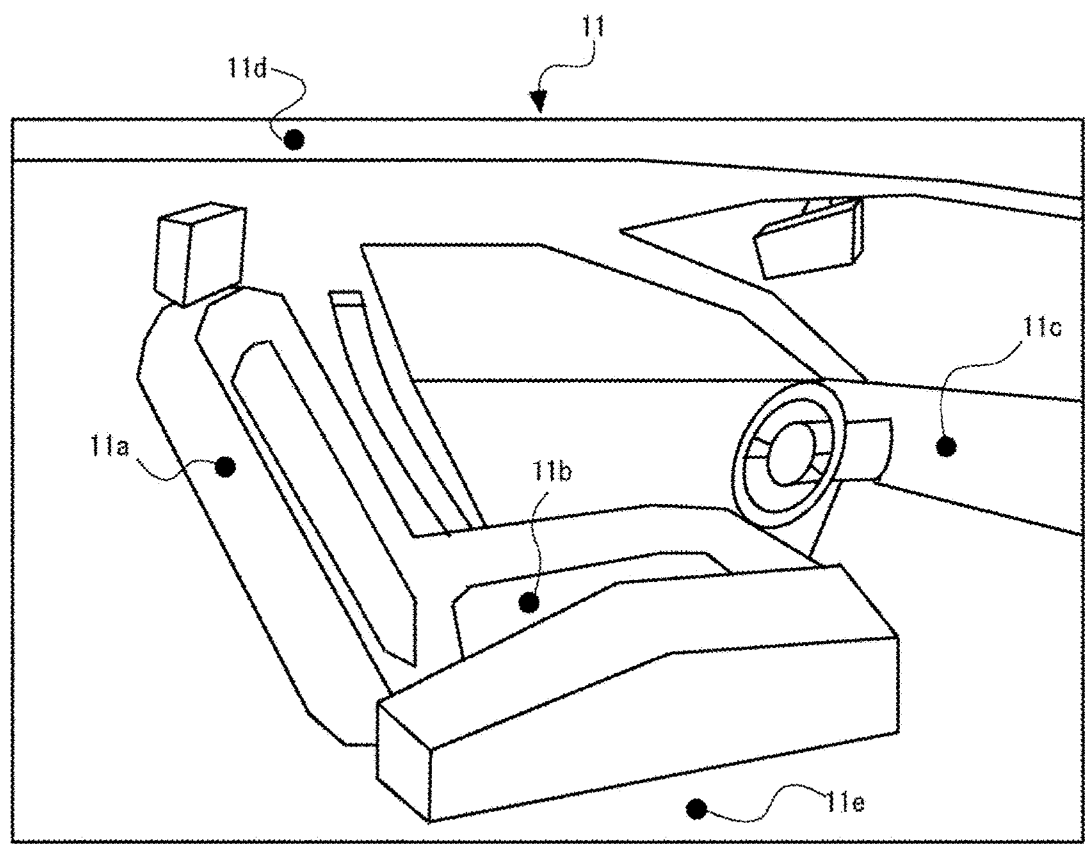
FIG. 3 is a perspective view of the interior of a vehicle having the sensor system, which is illustrated in FIG. 1, as a driver monitoring system.

FIG. 3 is a perspective view of the interior of a vehicle 11 having the sensor system 1 as a driver monitoring system.

When the vehicle 11 has the sensor system 1, the first sensor(s) 2 are disposed, for example, on the backrest 11*a*, the bottom 11*b* of a seat, the dashboard 11*c*, and the ceiling 11*d* of the vehicle's interior. A human body on the seat is the measurement target 5, and radio waves are radiated (emitted) to the human body. In this case, the first sensor(s) 2 detect body surface displacement of the human body as the predetermined displacement of the measurement target 5. The second sensor(s) 3 are disposed, for example, on the backrest 11*a*, the bottom 11*b* of the seat, and the floor 11*e* of the vehicle's interior. When a second sensor 3 is disposed on the backrest 11*a* or the bottom 11*b* of the seat, if the second sensor 3 is a vibration sensor, motions of the human body are detected as vibrations. If the second sensor 3 is a pressure sensor, body surface displacement of the human body is detected as the predetermined displacement of the measurement target 5 from pressure received by the pressure sensor from the human body. When a second sensor 3 is disposed on the floor 11*e* of the vehicle's interior, vibrations of the vehicle are detected as noise vibration data that is to be superimposed on body surface displacement data of the human body.

The configuration provides the vehicle 11 having the sensor system 1 which achieves a reduction of power consumption without changing accuracy of detection of the predetermined displacement such as body surface displacement.

Alternatively, the sensor system 1 may include a radio wave sensor included in a wearable device such as a smartwatch or a smartphone, a vibration or vital sensor, and a CPU. In this case, the radio wave sensor included in a wearable device or a smartphone, the vibration or vital sensor, and the CPU function as a first sensor 2, a second sensor 3, and the signal processing apparatus 4, respectively, which are illustrated in FIG. 1. For example, a program describing the flowchart in FIG. 2 is downloaded from the Internet or the like as an application, and is installed in a wearable device or a smartphone.

Figure 4:
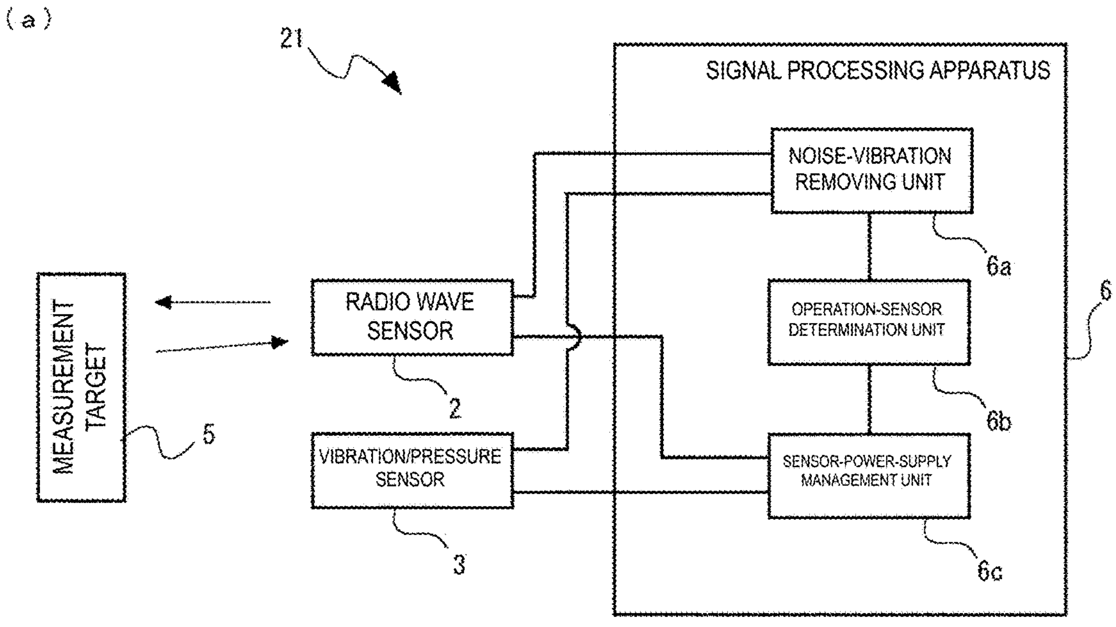
FIG. 4 includes a block diagram illustrating the schematic configuration of a sensor system according to a second exemplary embodiment of the present disclosure, and includes a block diagram illustrating the configuration of a noise-vibration removing unit.
Figure 4:
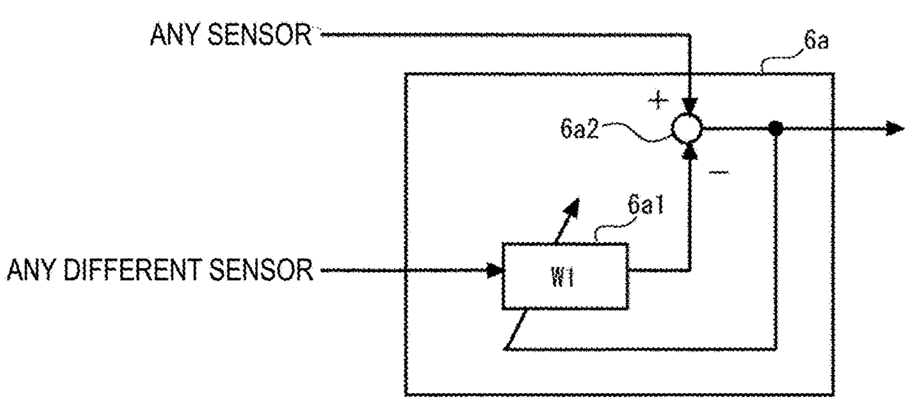

FIG. 4(*a*) is a block diagram illustrating the schematic configuration of a sensor system 21 according to a second exemplary embodiment of the present disclosure. The sensor system 21 is different from the sensor system 1 according to the first exemplary embodiment in that, instead of the signal processing apparatus 4 of the sensor system 1 according to the first exemplary embodiment, a signal processing apparatus 6 is included. The other points are substantially the same as those of the sensor system 1 according to the first exemplary embodiment.

The signal processing apparatus 6 includes a noise-vibration removing unit 6*a*, an operation-sensor determination unit 6*b*, and a sensor-power-supply management unit 6*c*.

The noise-vibration removing unit 6*a* performs computation of removing or attenuating, from predetermined-displacement data, noise vibration data superimposed as noise on the predetermined-displacement data, on the basis of predetermined-displacement data of the measurement target 5 and vibration data which are detected by the first sensor(s) 2 or the second sensor(s) 3. This computation is performed on multiple combinations of a first sensor(s) 2 and a second sensor(s) 3, multiple combinations of first sensors 2, or multiple combinations of second sensors 3.

The operation-sensor determination unit 6*b* determines, as operation sensors, any combination of sensors, which derives a value closest to the true value of the predetermined displacement among multiple pieces of predetermined displacement data obtained by the noise-vibration removing unit 6*a* removing noise vibration data. The operation sensors are minimal necessary sensors that are to be operated in view of removal or attenuation of noise vibration data superimposed on predetermined-displacement data.

The sensor-power-supply management unit 6*c* supplies power only to a combination of sensors which are to be determined as operation sensors by the operation-sensor determination unit 6*b*. Therefore, no power is supplied to the remaining sensors which are not determined as operation sensors. Like the sensor-power-supply management unit 4*b* of the sensor system 1 according to the first exemplary embodiment, the sensor-power-supply management unit 6*c* may control power supply by directly switching ON or OFF the power supply of each sensor, or by outputting, to each sensor, an instruction to switch ON or OFF the power supply.

The noise-vibration removing unit 6*a* may use blind source separation technique, such as independent component analysis (ICA) or independent vector analysis (IVA), in removal of vibration data. This technique enables noise vibration data to be separated from predetermined-displacement data such as body surface displacement with use of a combination of sensors which are determined as operation sensors. At that time, the dimensionality of predetermined-displacement data is represented by m in the SI unit system; the dimensionality of noise vibration data is represented by $m/s^2$ in the SI unit system. Thus, in the computation process by the noise-vibration removing unit 6*a*, after noise vibration data is integrated twice, independent component analysis or independent vector analysis is performed.

Alternatively, the noise-vibration removing unit 6*a* may use an adaptive filter using an algorithm such as LMS (Least Mean Square), in removal of vibration data. The adaptive filter enables separation, from predetermined-displacement data such as body surface displacement data which is received from any sensor determined as an operation sensor, of noise vibration data which is received from another sensor. FIG. 4(*b*) is a block diagram illustrating the circuit configuration of the noise-vibration removing unit 6*a* formed by using such an adaptive filter 6*a*1.

Noise, which is superimposed on predetermined-displacement data such as body surface displacement, is propagated over a distance away from the source before the superimposition, and thus receives influence from the transfer characteristics during the propagation. Therefore, the noise-vibration removing unit 6*a* obtains the difference between the predetermined-displacement data and the noise vibration data by using a subtractor 6*a*2, and feeds the difference, which is obtained from the output of the subtractor 6*a*2, back to the adaptive filter 6*a*1. The magnitude of the transfer factor W1 of the adaptive filter 6*a*1 is adjusted, and noise vibration data is separated from predetermined-displacement data to extract body surface displacement data or the like.

Alternatively, the noise-vibration removing unit 6*a* may use Demucs, Sepformer, Conv-TasNet, or the like, which is used in speech separation, or a machine learning technique, which is obtained through modification of such a technique, in removal of vibration data. These methods enable noise vibration data to be separated from predetermined-displacement data such as body surface displacement with use of a combination of sensors determined as operation sensors.

Figure 5:
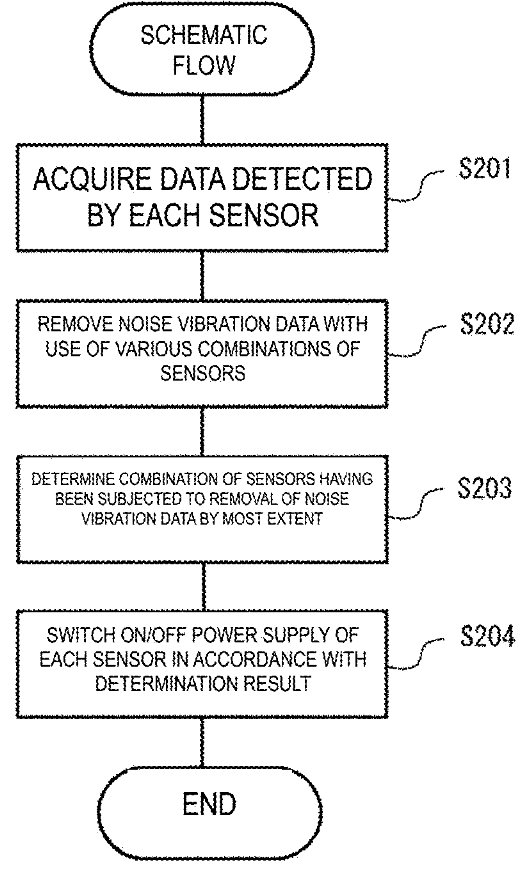
FIG. 5 is a flowchart of a power supply control process in a sensor system according to the second exemplary embodiment.

FIG. 5 is a flowchart of a power supply control process performed on the sensors in the sensor system 21 according to the second exemplary embodiment of the present disclosure. Steps S201 to S204 in the power supply control process are also performed according to a computer program, which is stored in a memory included in the signal processing apparatus 6, by a CPU included in the signal processing apparatus 6.

Detected-data acquisition step S201, in which data detected by each sensor is acquired, is first performed.

That is, also in detected-data acquisition step S201, like detected-data acquisition step S101 in FIG. 2, each first sensor 2 obtains predetermined-displacement data of the measurement target 5, for example, body surface displacement data or the like from a human body, from reflected waves obtained through reflection, from the measurement target 5, of radio waves emitted from the radio wave sensor to the measurement target 5. Each second sensor 3 obtains, for example, data of vibrations, which occur in or are transmitted to either one or both of the measurement target 5 and the first sensor(s) 2, or predetermined-displacement data of the measurement target 5, for example, body surface displacement data or the like of a human body.

Then, the noise-vibration removing unit 6*a* performs noise-vibration removing step S202 in which any vibration removal method described above is used to remove noise vibration data from predetermined-displacement data. This process is performed on various combinations of sensors, that is, multiple combinations of a first sensor(s) 2 and a second sensor(s) 3, multiple combinations of first sensors 2, or multiple combinations of second sensors 3.

The operation-sensor determination unit 6*b* performs operation-sensor determination step S203 in which a single combination of sensors, which detects predetermined-displacement data that is obtained through removal or attenuation of noise vibration data by the most extent and that is closest to the true value of the predetermined displacement, is determined from among multiple pieces of predetermined displacement data obtained in noise-vibration removing step S202 by removing or attenuating noise vibration data. This process is performed as follows.

That is, the operation-sensor determination unit 6*b* regards, as the main sensor, a single sensor that detects displacement data closest to the true value of predetermined-displacement data and that is any of the first sensor(s) 2 or any of the second sensor(s) 3 which detects predetermined-displacement data of the measurement target 5. Predetermined-displacement data, which is detected by the main sensor when the measurement target 5 is motionless, is stored in advance as reference data in a memory. Alternatively, data, which is predetermined as predetermined-displacement data obtained from the measurement target 5 which is motionless, is stored in advance as reference data in the memory. The operation-sensor determination unit 6*b* determines, as a combination of sensors which detects predetermined displacement data closest to the true value of the predetermined displacement, a combination of sensors which has detected, in a particular frequency band, predetermined-displacement data having the highest correlation with the reference data stored in the memory or predetermined-displacement data having similar statistics such as a kurtosis. The particular frequency band is a frequency band in which predetermined-displacement data is obtained. For example, when the predetermined-displacement data is body surface displacement data of a human body, the particular frequency band is the frequency band of 0 Hz to 10 Hz which includes that of breath and that of heartbeat, or the frequency band of 1 Hz to 10 Hz which includes only that of heartbeat. The combination of sensors is determined as operation sensors which are minimal necessary sensors that are to be operated in view of removal or attenuation of noise vibration data superimposed on predetermined-displacement data.

The sensor-power-supply management unit 6*c* performs sensor-power-supply setting step S204 in which the power supply of each sensor is switched ON or OFF in accordance with the determination result obtained by the operation-sensor determination unit 6*b*. That is, the sensor-power-supply management unit 6*c* switches ON only the power supplies of the combination of sensors determined as operation sensors by the operation-sensor determination unit 6*b*, and switches OFF the power supplies of the remaining sensors.

The sensor system 21 according to the second exemplary embodiment performs computation of removing or attenuating noise vibration data, which is superimposed on predetermined-displacement data of the measurement target 5, from the predetermined-displacement data on the basis of predetermined-displacement data and vibration data which are detected by any combination of sensors. This computation is performed by the noise-vibration removing unit 6*a* on various combinations of sensors in noise-vibration removing step S202. In operation-sensor determination step S203, the operation-sensor determination unit 6*b* determines, as operation sensors, any combination which derives a value closest to the true value of the predetermined displacement among multiple pieces of predetermined-displacement data obtained through removal of noise vibration data performed by the noise-vibration removing unit 6*a*. Operation sensors are minimal necessary operation sensors that are to be operated in view of removal or attenuation of noise vibration data superimposed on predetermined-displacement data. In sensor-power-supply setting step S204, the sensor-power-supply management unit 6*c* supplies power only to the combination of sensors determined as operation sensors by the operation-sensor determination unit 6*b*.

Therefore, even when the sensor system 21 includes multiple first and second sensors 2 and 3 to improve accuracy of detection of the measurement target 5's predetermined displacement, power is supplied, not to all the sensors, but only to minimal necessary sensors that are to be operated in view of removal or attenuation of noise vibration data superimposed on predetermined-displacement data. Therefore, even when multiple first and second sensors 2 and 3 are used to improve accuracy of detection of the measurement target 5's predetermined displacement, the power consumption of the sensor system 21 may be reduced without changing the detection accuracy.

The sensor system 21 according to the second exemplary embodiment may be also applied to a driver monitoring system by appropriately disposing the first sensor(s) 2 and the second sensor(s) 3 in the interior of the vehicle 11 as described by using FIG. 3. In this case, the vehicle 11, which has the sensor system 21 achieving a reduction of power consumption, may be provided without changing accuracy of detection of the predetermined displacement such as body surface displacement.

Figure 6:
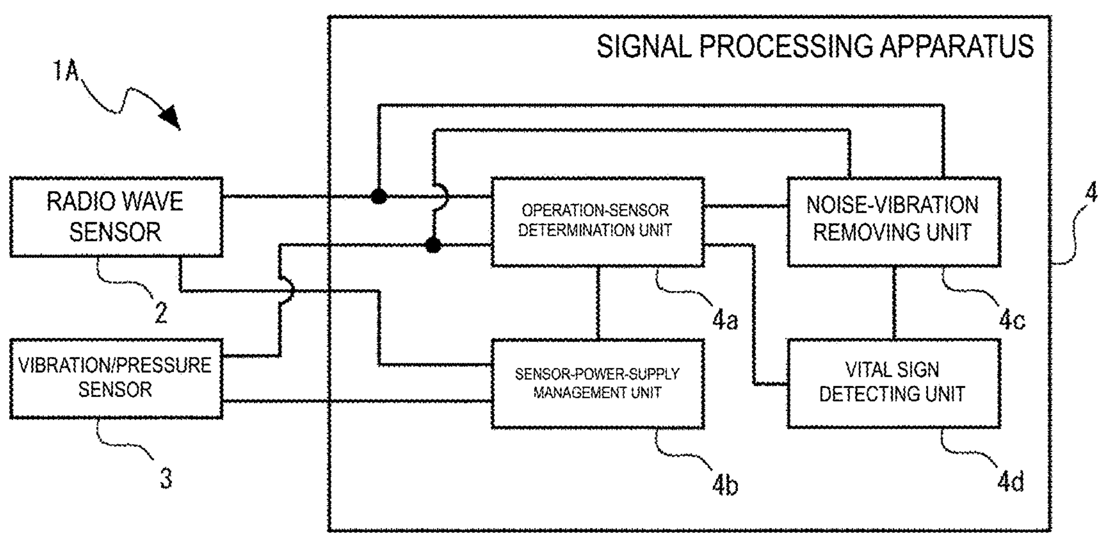
FIG. 6 is a block diagram illustrating the schematic configuration of a sensor system according to a third exemplary embodiment of the present disclosure.

FIG. 6 is a block diagram illustrating the schematic configuration of a sensor system 1A according to a third exemplary embodiment of the present disclosure. The sensor system 1A is different from the sensor system 1 according to the first exemplary embodiment in that the signal processing apparatus 4 includes a noise-vibration removing unit 4*c* and a vital sign detecting unit 4*d* and that the measurement target 5 is a human body. The other points are substantially the same as those of the sensor system 1 according to the first exemplary embodiment.

The noise-vibration removing unit 4*c* performs computation of removing or attenuating noise vibration data, which is detected by a combination of sensors determined as operation sensors by the operation-sensor determination unit 4*a*, from body surface displacement data detected as the predetermined displacement by the combination. If the determination result of noise-vibration-detecting-sensor determination step S103 in FIG. 2 is Yes, which indicates that a sensor having obtained noise vibration data is present, this computation is performed on the combination of sensors determined as operation sensors by the operation-sensor determination unit 4*a* in operation-sensor second-determination step S105.

The vital sign detecting unit 4*d* detects vital signs of a human body from body surface displacement data obtained through removal or attenuation of noise vibration data performed by the noise-vibration removing unit 4*c*. Examples of vital signs include the heart rate, the heart rate variability, the respiratory rate, and the depth of breathing of a human body which is the measurement target 5.

If the determination result of noise-vibration-detecting-sensor determination step S103 in FIG. 2 is No, which indicates that no sensors have obtained noise vibration data, and the main sensor is determined as an operation sensor in operation-sensor first-determination step S104, the vital sign detecting unit 4*d* detects vital signs of a human body from body surface displacement data of the human body which is detected as the predetermined displacement by the main sensor. In this case, the noise-vibration removing unit 4*c* is not used.

In the sensor system 1A according to the third exemplary embodiment, the noise-vibration removing unit 4*c* removes or attenuates noise vibration data, which is detected by a combination of sensors determined as operation sensors in step S105, from body surface displacement data, which is detected by the combination, and the vital sign detecting unit 4*d* detects vital signs of a human body. Alternatively, the vital sign detecting unit 4*d* detects vital signs of a human body, not through the noise-vibration removing unit 4*c*, from body surface displacement data which is detected by the main sensor determined as an operation sensor in step S104 and from which noise vibration data has been removed or attenuated. Therefore, the sensor system 1A enables vital signs of a human body to be detected without degrading accuracy of detection of a human body's vital signs and with low power consumption.

The sensor system 1A according to the third exemplary embodiment may be also applied to a driver monitoring system by appropriately disposing the first sensor(s) 2 and the second sensor(s) 3 in the interior of the vehicle 11 as described by using FIG. 3. In this case, the vehicle 11, which has the sensor system 1A achieving a reduction of power consumption, may be provided without degrading performance of estimation of a human body's vital signs.

Figure 7:
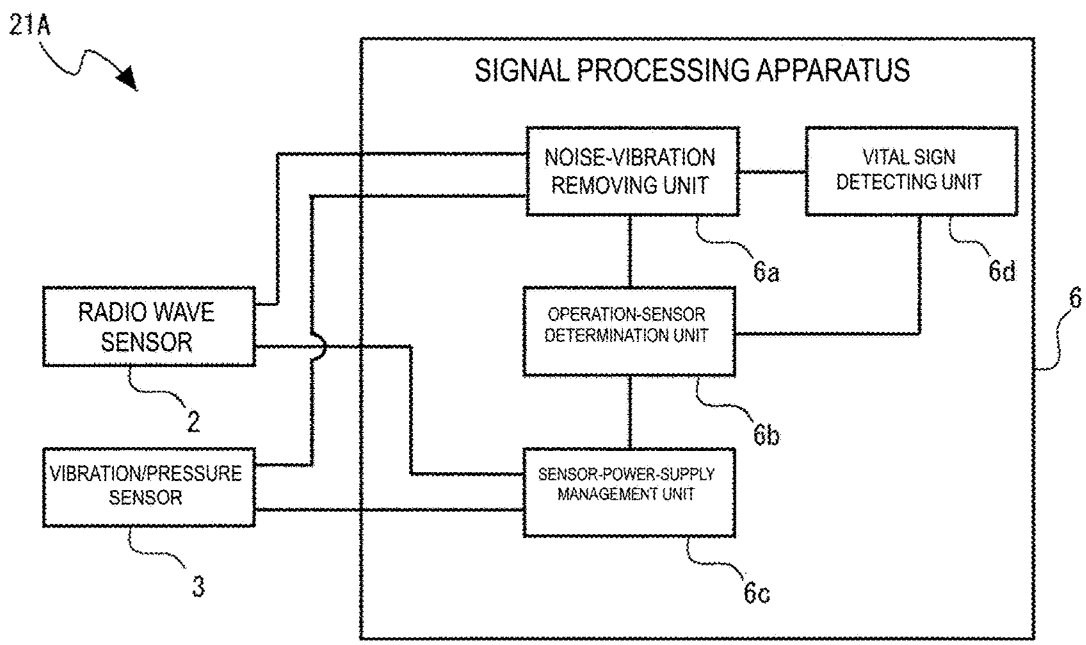
FIG. 7 is a block diagram illustrating the schematic configuration of a sensor system according to a fourth exemplary embodiment of the present disclosure.

FIG. 7 is a block diagram illustrating the schematic configuration of a sensor system 21A according to a fourth exemplary embodiment of the present disclosure. The sensor system 21A is different from the sensor system 21 according to the second exemplary embodiment in that the signal processing apparatus 6 includes a vital sign detecting unit 6*d* and that the measurement target 5 is a human body. The other points are substantially the same as those of the sensor system 21 according to the second exemplary embodiment.

The vital sign detecting unit 6*d* detects vital signs of a human body from body surface displacement data, which is obtained through computation using a combination of sensors determined as operation sensors by the operation-sensor determination unit 6*b*, from among multiple pieces of body surface displacement data from which noise vibration data has been removed or attenuated by the noise-vibration removing unit 6*a*. The sensor system 21A according to the fourth exemplary embodiment enables vital signs of a human body to be detected without degrading accuracy of detection of the human body's vital signs and with low power consumption.

The sensor system 21A according to the fourth exemplary embodiment may be also applied to a driver monitoring system by appropriately disposing the first sensor(s) 2 and the second sensor(s) 3 in the interior of the vehicle 11 as described by using FIG. 3. Also in this case, the vehicle 11, which has the sensor system 21A achieving a reduction of power consumption, may be provided without degrading performance of estimation of a human body's vital signs.

Figure 8:
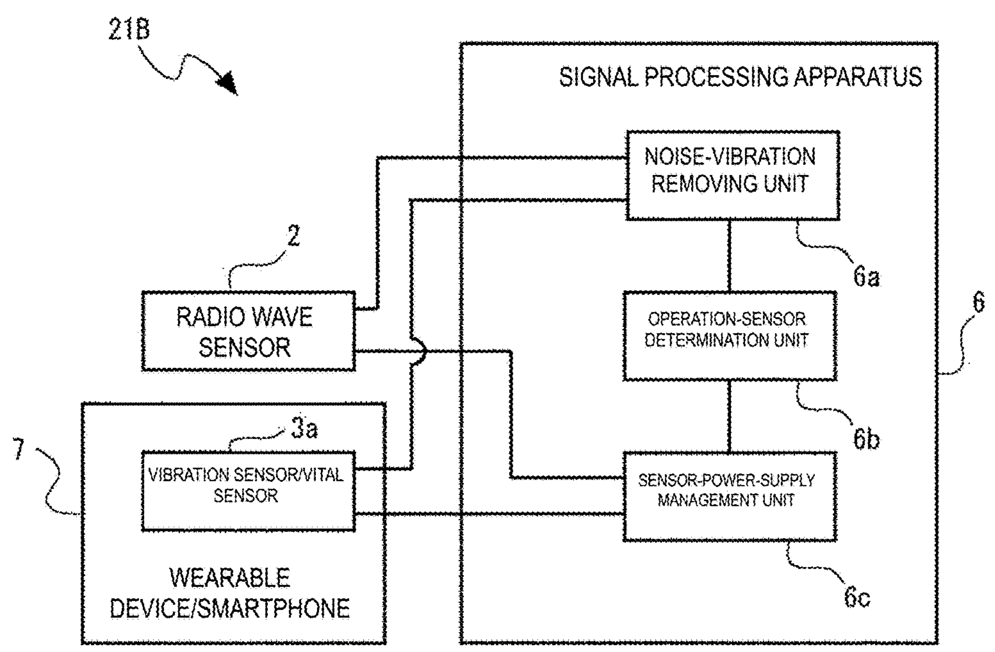
FIG. 8 is a block diagram illustrating the schematic configuration of a sensor system according to a fifth exemplary embodiment of the present disclosure.

FIG. 8 is a block diagram illustrating the schematic configuration of a sensor system 21B according to a fifth exemplary embodiment of the present disclosure. The sensor system 21B is different from the sensor system 21 according to the second exemplary embodiment in that a second sensor 3 in the sensor system 21 according to the second exemplary embodiment is formed of a vibration or vital sensor 3*a* included in a wearable device, such as a smartwatch, or smartphone 7, and that the measurement target 5 is a human body. The other points are substantially the same as those of the sensor system 21 according to the second exemplary embodiment. The vital sensor 3*a* included in the wearable device or smartphone 7 is a sensor which obtains vital signs, such as a PPG sensor (photoplethysmography sensor) or an ECG sensor (electrocardiogram sensor).

The wearable device or smartphone 7 is not limited to these. The wearable device or smartphone 7 may be any as long as it is a portable device having a function of communicating with the vibration or vital sensor 3*a*. In the configuration, the vibration or vital sensor 3*a* communicates with the signal processing apparatus 6, for example, through wireless communication such as Bluetooth® or wired communication. In the fifth exemplary embodiment, the sensor-power-supply management unit 6*c* switches ON or OFF the communication between the vibration or vital sensor 3*a* and the signal processing apparatus 6 without switching ON or OFF the power supply of the vibration or vital sensor 3*a*. The power supply of the vibration or vital sensor 3*a* is switched ON or OFF in accordance with the situation on the wearable device or smartphone 7 side.

In the sensor system 21B according to the fifth exemplary embodiment, the vibration or vital sensor 3*a* included in the wearable device or smartphone 7 detects noise vibration data, which is superimposed on body surface displacement data, or body surface displacement data of the measurement target 5. Therefore, the configuration of the sensor system 21B is simplified by the use of the vibration or vital sensor 3*a*. Thus, the power consumption of the sensor system 21B may be reduced with lowering the product price of the sensor system 21B and without changing accuracy of detection of body surface displacement.

Like the sensor system 21B according to the fifth exemplary embodiment, the sensor system 1 according to the first exemplary embodiment, the sensor system 21A according to the third exemplary embodiment, and the sensor system 21B according to the fourth exemplary embodiment may have configurations in which a second sensor 3 is formed by the vibration or vital sensor 3*a* included in the wearable device, such as a smartwatch, or smartphone 7. Also in this case, operational effect substantially the same as that of the sensor system 21B according to the fifth exemplary embodiment is exerted.

The sensor system 21B according to the fifth exemplary embodiment may be also applied to a driver monitoring system by appropriately disposing the first sensor(s) 2 and the wearable device or smartphone 7, which includes the vibration or vital sensor 3*a*, in the interior of the vehicle 11 as described by using FIG. 3. Also in this case, the vehicle 11, which has the sensor system 21B achieving a reduction of power consumption, may be provided without degrading performance of estimation of a human body's vital signs.

REFERENCE SIGNS LIST

1, 1A, 21, 21A, 21B sensor system
2 first sensor
3 second sensor
3*a* vibration or vital sensor
4, 6 signal processing apparatus
4*a*, 6*b* operation-sensor determination unit
4*b*, 6*c* sensor-power-supply management unit
4*c*, 6*a* noise-vibration removing unit
4*d*, 6*d* vital sign detecting unit
5 measurement target
7 wearable device or smartphone

The invention claimed is:

1. A sensor system comprising:
one or more first sensors that emit electromagnetic waves to a measurement target, and that receive reflected waves to detect predetermined-displacement data of the measurement target, the reflected waves being obtained through reflection of the electromagnetic waves from the measurement target;
one or more second sensors that detect vibration data, the vibration occurring in or being transmitted to at least one of the measurement target or the one or more first sensors;
an operation-sensor determination circuit that, on the basis of the predetermined-displacement data and the vibration data, determines a minimal necessary operation sensor from the one or more first sensors or the one or more second sensors which is to be operated in view of removal or attenuation of noise vibration data superimposed as noise on the predetermined-displacement data; and
a sensor-power-supply management circuit that supplies power only to the operation sensor.

2. The sensor system according to claim 1,
wherein the operation sensor corresponds to a single first sensor and a single second sensor.

3. The sensor system according to claim 1,
wherein the operation sensor corresponds to a combination of a single first sensor and a plurality of second sensors.

4. The sensor system according to claim 1,
wherein the operation sensor corresponds to a combination of a plurality of first sensors and a single second sensor.

5. The sensor system according to claim 1,
wherein the operation sensor corresponds to a combination of a plurality of first sensors and a plurality of second sensors.

6. The sensor system according to claim 1,
wherein, when any of the first and second sensors does not detect the noise vibration data, the operation-sensor determination circuit determines only the one or more first sensors or the one or more second sensors as the operation sensor.

7. The sensor system according to claim 6,
wherein the measurement target is a human body, and
wherein the sensor system further comprises
a vital sign detecting circuit that detects a vital sign of the human body from body surface displacement data detected as the predetermined-displacement data by the operation sensor.

8. The sensor system according to claim 1,
wherein a total of the one or more first sensors and the one or more second sensors is three or more, and
wherein the operation-sensor determination circuit determines, as the operation sensors, a combination of one or more of the one or more first sensors or one or more of the one or more second sensors which detect the predetermined-displacement data and the noise vibration data, and different one or more of the one or more first sensors or different one or more of the one or more second sensors which detect the noise vibration data.

9. The sensor system according to claim 8,
wherein the measurement target is a human body, and
wherein the sensor system further comprises
a noise-vibration removing circuit that removes or attenuates the noise vibration data from body surface displacement data which is detected as the predetermined-displacement data by the operation sensors, the noise vibration data being detected by the operation sensors, and
a vital sign detecting circuit that detects a vital sign of the human body from the body surface displacement data obtained through removal or attenuation of the noise vibration data.

10. The sensor system according to claim 1,
wherein a total of the one or more first sensors and the one or more second sensors is three or more, and
wherein the operation-sensor determination circuit determines, as the operation sensors, a combination of one or more of the one or more first sensors or one or more of the one or more second sensors which detect the predetermined-displacement data and the noise vibration data, and different one or more of the one or more first sensors or different one or more of the one or more second sensors which detect the predetermined-displacement data and the noise vibration data.

11. The sensor system according to claim 1,
wherein the one or more second sensors correspond to a vibration sensor included in a wearable device or a smartphone.

12. The sensor system according to claim 11, wherein the wearable device is a smartwatch.

13. The sensor system according to claim 1,
wherein the one or more second sensors correspond to a vital sensor included in a wearable device or a smartphone.

14. A vehicle including the sensor system according to claim 1.

15. A sensor system comprising:

one or more first sensors that emit electromagnetic waves to a measurement target, and that receive reflected waves to detect predetermined-displacement data of the measurement target, the reflected waves being obtained through reflection of the electromagnetic waves from the measurement target;

one or more second sensors that detect vibration data, the vibration occurring in or being transmitted to at least one of the measurement target or the one or more first sensors;

a noise-vibration removing circuit that performs computation of removing or attenuating noise vibration data from the predetermined-displacement data on the basis of the predetermined-displacement data and the vibration data, the noise vibration data being superimposed as noise on the predetermined-displacement data, the computation being performed on a plurality of combinations from the one or more first sensors and the one or more second sensors, a plurality of combinations from the one or more first sensors, or a plurality of combinations from the one or more second sensors;

an operation-sensor determination circuit that determines any of the combinations as minimal necessary operation sensors which are to be operated in view of removal or attenuation of the noise vibration data, the any of the combinations deriving a value closest to a true value of the predetermined-displacement data among a plurality of pieces of predetermined-displacement data obtained through removal or attenuation of the noise vibration data, the operation sensors being from the one or more first sensors or the one or more second sensors; and a sensor-power-supply management circuit that supplies power only to the operation sensors.

16. The sensor system according to claim 15, wherein the measurement target is a human body, and wherein the sensor system further comprises a vital sign detecting circuit that detects a vital sign of the human body from body surface displacement data obtained through computation with use of the operation sensors.

17. The sensor system according to claim 15, wherein the operation sensor corresponds to a combination of a plurality of first sensors and a plurality of second sensors.

18. The sensor system according to claim 15, wherein the operation sensor corresponds to a combination of a single first sensor and a plurality of second sensors.

19. The sensor system according to claim 15, wherein the operation sensor corresponds to a combination of a plurality of first sensors and a single second sensor.

20. A vehicle including the sensor system according to claim 15.

* * * * *